(12) United States Patent
Leistner et al.

(10) Patent No.: US 7,311,845 B2
(45) Date of Patent: Dec. 25, 2007

(54) ADSORBING MATERIAL FOR BLOOD AND PLASMA CLEANING METHOD AND FOR ALBUMIN PURIFICATION

(75) Inventors: Aniela Leistner, Birkenstein (DE); André Leistner, Birkenstein (DE)

(73) Assignee: Polymerics GmbH, Berlin (DE)

( * ) Notice: Subject to any disclaimer, the term of this patent is extended or adjusted under 35 U.S.C. 154(b) by 20 days.

(21) Appl. No.: 10/540,823

(22) PCT Filed: Dec. 29, 2003

(86) PCT No.: PCT/DE03/04297

§ 371 (c)(1),
(2), (4) Date: Jun. 23, 2005

(87) PCT Pub. No.: WO2004/060554

PCT Pub. Date: Jul. 22, 2004

(65) Prior Publication Data

US 2006/0058413 A1    Mar. 16, 2006

(30) Foreign Application Priority Data

Dec. 30, 2002  (DE) ............................... 102 61 910

(51) Int. Cl.
*B01D 15/00* (2006.01)
(52) U.S. Cl. ............ 210/692; 210/502.1; 502/402
(58) Field of Classification Search ........... 210/692, 210/502.1; 502/402; 521/29, 38; 604/5.04
See application file for complete search history.

(56) References Cited

U.S. PATENT DOCUMENTS

| | | | |
|---|---|---|---|
| 3,794,584 A | 2/1974 | Kunin et al. | 210/692 |
| 4,048,046 A | 9/1977 | MacMullin | 204/266 |
| 4,171,283 A | 10/1979 | Nakashima et al. | 502/402 |
| 4,202,775 A | 5/1980 | Abe et al. | 210/287 |
| 5,420,601 A | 5/1995 | Amano | 345/60 |
| 5,773,384 A | 6/1998 | Davankov et al. | 502/402 |
| 6,177,513 B1 | 1/2001 | Takeuchi et al. | 525/54.1 |
| 6,419,830 B2 | 7/2002 | Strom et al. | 210/645 |
| 6,423,024 B1 | 7/2002 | Strom et al. | 604/8 |
| 2003/0027879 A1* | 2/2003 | Davankov et al. | 521/82 |

FOREIGN PATENT DOCUMENTS

| | | |
|---|---|---|
| DE | 249274 | 9/1987 |
| DE | 19922268 | 11/2000 |
| EP | 0319144 | 6/1989 |
| SU | 732207 | 5/1980 |
| SU | 844569 | 7/1981 |
| WO | WO 02059184 | 8/2002 |

\* cited by examiner

*Primary Examiner*—Matthew O. Savage
(74) *Attorney, Agent, or Firm*—Collard & Roe, P.C.

(57) ABSTRACT

The invention relates to an adsorbent material, a method for cleaning blood and plasma and purifying albumin, and to a method for producing said adsorbent material. The inventive adsorbent material is embodied in the form of a highly cross-linked and porous spherical divinylbenzene copolymer which contains from 4 to 30 weight % of an imidazole derivative and at least 50 weight % of divinylvenzene incorporated by radical polymerization in the presence of air and/or oxygen. Said adsorbent material is embodied in such a way that it is biocompatible and suitable for removing free and albumin-bound toxic substances, drugs, pharmaceutical products, endogenic and exogenic toxins from blood, plasma, and external albumin circuits at a high rate and efficiency. The material is used in particular for adsorbing bilirubin and bile acids and is produced by suspension polymerization.

12 Claims, 2 Drawing Sheets

Particle shape and particle size distribution of the adsorbent material of example Particle shape and particle size distribution of the adsorbent material of example Comparison of activated charcoal and adsorbent material AM1 in the static (fig. 2a) and dynamic (fig. 2b) bilirubin adsorption test

ADSORBING MATERIAL FOR BLOOD AND PLASMA CLEANING METHOD AND FOR ALBUMIN PURIFICATION

CROSS REFERENCE TO RELATED APPLICATIONS

Applicants claim priority under 35 U.S.C. § 119 of German Application No. 102 61 910.7 filed on Dec. 30, 2002. Applicants also claim priority under 35 U.S.C. § 365 of PCT/DE2003/004297 filed on Dec. 29, 2003. The international application under PCT article 21(2) was not published in English.

The present invention relates to an adsorbent material for methods of blood, blood plasma, and albumin purification as well as a method for producing said material.

Fields of application of this invention are special medical and pharmaceutical methods for the purification of blood, blood plasma, and albumin, which remove free and albumin-bound toxins from blood, blood plasma, and albumin. These methods are used to treat poisoning with pharmaceuticals and drugs, poisoning with chemicals and highly dosed drugs for chemotherapy, acute and chronic kidney failure, acute and chronic liver failure (e.g. hyperbilirubinemia, cholestasis, hepatic encephalopathy, fulminate liver failure), and multiple organ failure.

Conventional methods of blood purification are divided into membrane techniques (hemodialysis, plasmapheresis, ultrafiltration), adsorption techniques (hemoperfusion, plasmaperfusion), and combined membrane-adsorption techniques (e.g. MARS®).

Membrane techniques remove unwanted substances from a liquid mixture by bringing the mixture in contact with a rinsing solution trough a semi permeable membrane where the rinsing solution is free from the substance to be removed (dialysis). The concentration difference of the unwanted substance between the mixture and the rinsing solution is the driving force for concentration equilibration. If the pore size of the semipermeable membrane is such that the unwanted substance can pass through it then concentration equilibration will occur by permeation of the unwanted substance into the rinsing solution. In hemolysis membranes are used whose pores are wide enough for the toxins to be removed and at the same time small enough to retain blood components with bigger molecular dimensions such as albumin, hemoglobin, erythrocytes, leukocytes, and thrombocytes.

In adsorption techniques (hemo perfusion, plasma perfusion), blood or blood plasma flows through a column or cartridge which is filled with a macroporous material such as activated charcoal, an adsorbent polymer, or ion exchanger, and is thereby detoxified. In plasma perfusion blood cells have to be separated before the adsorption step and reunited with the plasma after treatment.

The MARS method belongs to the combined techniques of extracorporeal blood purification comprising a combination of dialysis and perfusion. In the MARS method, the patient's blood flows through an albumin dialyser and then back to the patient. A pure albumin solution with a concentration of 5 to 20% circulates on the wash side of the albumin dialyser. Since most blood toxins are bound to albumin this creates the driving force for the toxins to pass through the dialyser membrane. After passing the albumin dialyser the albumin solution is purified in an in-line perfusion block followed by a standard dialyser and then returned to the albumin dialyser. With this principle it is possible to replace the detoxifying function of the liver which is life-threatening in liver failure.

Hemo dialysis, ultrafiltration and plasma pheresis separate blood compounds according to their size and mostly unselectively. In contrast to this, sorption techniques can work selectively as well as less selectively. Membrane techniques require tailored membranes, and sorption techniques require tailored adsorbents.

For extracorporeal blood purification methods activated charcoal is used as an adsorbent as well as increasingly synthetic, macroporous adsorbent polymers. Disadvantages of charcoal are the driving force for this development. These include low mechanical stability, low selectivity and low adsorption speed, further high retention of white blood cells and blood platelets, and initiation of blood clots.

In the literature, the following polymer adsorbents are described:
1. porous and highly porous styrene-divinylbenzene copolymers,
2. macroporous divinylbenzene copolymers,
3. macroporous methacrylate and acrylate co- and ter-polymers, respectively,
4. porous, pearl-shaped cellulose derivatives.

SU 732207 describes sorbents produced from activated charcoal and coated activated charcoal, e.g. with a solution of poly(acrylic acid) or poly(acrylic acid) and poly(ethylene amine). Further polymer coatings of activated charcoals are described in U.S. Pat No. 4,048,046, U.S. Pat. No. 4,171,283, U.S. Pat. No. 5,420,601, and SU 844569. However, the disadvantages of activated charcoal such as low mechanical stability and low adsorption speed could not be eliminated with these methods.

Macroporous styrene-divinylbenzene copolymers have been used to remove barbiturates and glucothimides from dog blood in 1974 according to U.S. Pat. No. 3,794,584. However, it has been shown later, that these materials are highly non-polar, non-selective, and incompatible with blood. Highly porous styrene-divinylbenzene copolymers with a specific surface greater than 800 $m^2/g$, obtained by post-crosslinking of weakly cross-linked styrene-divinylbenzene copolymers using monochloro dimethyl ether in the presence of Friedel-Crafts catalysts, were also described 12 years later in 1986 as especially effective and fast-adsorbing materials for hemo perfusion in DD 249274A1. These adsorbents also show insufficient blood compatibility and require additional post-treatment. Furthermore, their production is accompanied by high risks for humans and environment because of the use of carcinogenic monochloro dimethyl ether.

Special, complex modification of the surface of highly porous styrene-divinylbenzene copolymers with trifluoralkoxyphosphazenes (U.S. Pat. No. 5,773,384) can improve blood compatibility. However, additional modification decreases the specific surface and pore accessibility as well as enormously increases the purification efforts since all remaining reagents and catalysts must be removed from the macro, meso, and micropores of the polymer prior to use in hemo perfusion.

Surface modification of highly crosslinked divinylbenzene copolymers by coating or grafting polymerization is described in recently filed patent applications U.S. Pat. No. 6,419,830 (2001) and U.S. Pat. No. 6,423,024 (2002) to produce highly porous, spherical divinylbenzene resins for the adsorption of health-threatening substances such as β-2-microglobuline from blood or plasma. The coating is performed on commercially available, highly porous divinylbenzene copolymers consisting of 60 to 90% divinylbenzene, having a specific surface of 200 to 1600 $m^2/g$, pore sizes from 20 to 500 Å, total pore volume up to 2.5 ml/g and particle sizes from 25 to 2500 µm. The hemocompatible coatings are obtained by reaction of residue vinyl groups on the surface of the DVB copolymer with hemocompatible monomers or polymers comprising phosphatidylcholine, heparin, polyalkylene glykolene, polyalkoxyphosphazenes, and poly(vinyl pyrrolidone). Other coatings claimed consist of various vinylpyridine-, vinylimidazole-, and vinylpyrrolidone-derivatives as well as various derivatives of acrylic acid and methacrylic acids. The obvious disadvantage of these methods is that the hemocompatible coating is applied subsequently, thereby leading to a reduction in specific surface and pore accessibility as described above. Further disadvantages comprise the complete removal of the monomers used for the coating which are often considered harmful or even carcinogenic. Therefore, the purification of polymers modified using these methods to be hemocompatible is complex, expensive and not quite risk-free.

On the other hand, coatings applied from polymer solutions often have the disadvantage that they can be partially dissolved in aqueous isotonic solutions of sodium chloride or in body fluids and thus enter the blood circuit of a patient in an uncontrolled way.

Thus, there is need for an essentially spherical, biocompatible adsorbent material suitable for the removal of albumin-bound toxins, drugs, pharmaceuticals, endogenic and exogenic toxins from blood, blood plasma or albumin circuits, having high adsorption speed and capacity. Furthermore there is need for a method to produce said adsorbent material in a relatively simple and economical way.

DETAILED DESCRIPTION OF THE INVENTION

Figure 1:
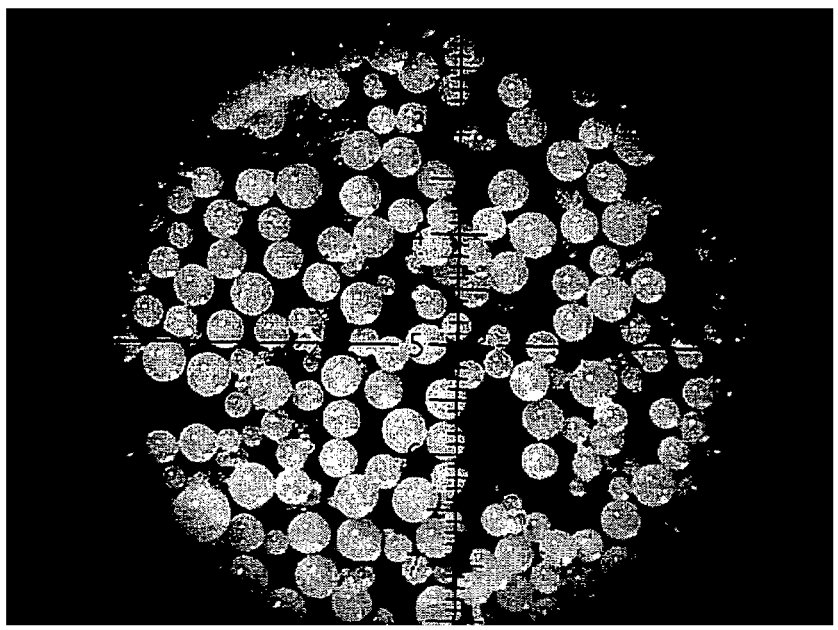
FIG. 1 is a picture of the inventive absorbent particles.

The present invention provides an adsorbent material consisting of a highly cross-linked, highly porous, particulate or spherical divinylbenzene copolymer comprising 4 to 30 weight % of one or multiple substituted or unsubstituted vinylimidazole monomers, 50 to 85 weight % of divinylbenzene (DVB) and 5 to 40 weight % of ethylvinylbenzene, all incorporated into the polymer network by polymerization. Suitable vinylimidazole monomers are 1-vinylimidazole and/or 4-vinylimidazole exclusively or in mixture. Further suitable vinylimidazole monomers comprise 1-vinyl-2-methylimidazole, 1-vinyl-2-ethylimidazole, 1-propenyl-2-methylimidazole, and 1-allyl-2-methylimidazole, exclusively or in various mixtures with each other or with unsubstituted vinylimidazole monomers. The content of the imidazole monomers in the adsorbent polymer of this invention can be varied in a wide range, preferably between 5 and 20 mole %. Suitable divinylbenzene monomers are commercially available solutions of divinylbenzene comprising 60 to 80 weight % divinylbenzene isomers and 40 or 20 weight % of various isomers of ethylvinylbenzene.

The adsorbent material of this invention has an optimized specific surface in the range from 200 to 900 $m^2/g$ and an optimized pore size distribution with a total pore volume from 1.0 to 2.0 $cm^3/g$. Preferred embodiments of this invention comprise up to 0.3 $cm^3/g$ micropores, up to 1.2 $cm^3/g$ mesopores and up to 0.5 $cm^3/g$ macropores. According to IUPAC (International Union of Pure and Applied Chemistry) micropores are defined as pores with pore diameters below 20 Å, mesopores are pores between 20 Å and 500 Å, and macropores are pores with diameters greater than 500 Å. For the adsorbent material of this invention the preferred average pore size is in the range from 100 to 500 Å, preferably 300 Å.

Furthermore, the adsorbent material has a particle size distribution from 50 to 300 µm, especially if it is intended to be used in a perfusion method or in the MARS process. The particles can also be produced in a size from 1 to 50 µm to be used in novel alternate plasma- and blood purification methods. It is a particular advantage that the particles are predominantly spherical and that they can be produced with a narrow particle size distribution.

The adsorbent material of this invention is produced by suspension polymerization in the presence of selected inert substances and suspension stabilizers. The inert substances are removed from the polymer after polymerization. In conjunction with the DVB they are responsible for the degree of porosity, i.e. for the pore size distribution and pore volume. Suitable inert substances comprise aliphatic and aromatic hydrocarbons, higher molecular alcohols, esters or suitable polymer solutions. Preferred inert substances of this invention comprise toluene, dichlormethane, carbon tetrachloride, butyl acetate, ethyl acetate, exclusively or as a mixture. The content of the inert substance in the organic phase can be varied in the range from 25 to 50 weight %.

The function of the suspension stabilizer is to prevent coagulation of the droplets during polymerization. Suitable suspension stabilizers of this invention comprise water-soluble synthetic and natural polymers, e.g. poly(vinyl alcohol), partly saponified poly(vinyl acetate), methyl cellulose, hydroxyethyl cellulose, polyacrylic acid sodium salts, carboxymethyl cellulose sodium salt, and furthermore Pickering stabilizers such as calcium phosphate, bentonite, montmorillonite, aluminium hydroxide, magnesium hydroxide, and calcium carbonate.

The suspension polymerization is initiated by a monomer soluble, radical initiator. Suitable initiators of this invention comprise dibenzoyl peroxide, methylethylketone peroxide, and azoisobutyronitrile. Preferably, the amount of initiator is in the range of 0.2 to 2.0 weight % with respect to the monomer mixture.

In comparison with conventional activated charcoal and other commercial adsorbents the adsorbent material of this invention displays much higher adsorption capacity and adsorption speed of free and albumin-bound toxins and poisons, particularly—as shown in the following examples—for bilirubin-albumin complexes (B-HSA solutions) and for free bile acids.

Furthermore, the adsorbent material of this invention also adsorbs N-acetyl tryptophane, octane acids, fatty acids, phenols, and caffeine, at much higher speed and capacity than other commercially available adsorbent materials. Moreover, the adsorbent material of this invention exhibits good biocompatibility as has been shown in cytotoxicological and hemolysis tests. The adsorbent material can be sterilized without changing its advantageous properties and due to its good mechanical stability it can be treated without wear debris. When applied in columns or cartridges it shows advantageous flow behaviour so that flow rates up to 200 ml/min are possible. The adsorbent material of this invention has been tested in solutions of bilirubin and human serum albumin in both batch tests (static bilirubin test) and under circulating conditions (dynamic bilirubin test).

The invention is further illustrated by the following examples.

EXAMPLE 1

Preparation of the Adsorbent Material (AM1)

0.28 g poly(vinyl alcohol) with a molecular weight of 49000 g/mole were dissolved in 142.5 g deionized water at 30° C. in a heated 250 ml cylindrical vessel equipped with a KPG stirrer, reflux condenser, thermometer and two baffles. 7.5 g NaCl were added and the solution heated to 70° C. The stirring speed was set to 650 rpm. The monomer solution, comprising 18.7 g divinylbenzene, 12.5 g 1-vinylimidazole, 18.7 g ethyl acetate and 0.25 g AIBN was added at once. The emulsion was stirred for 60 min at 70° C. until a stable droplet size was established and then heated to 80° C. and polymerized at this temperature for 10 h. The obtained suspension was then cooled to room temperature and filtered on a suction filter. The filter cake was washed with 3 bed volumes of deionized water and then with 2 bed volumes of ethanol. The filter cake was then dried for 12 at 100° C. in vacuo.

The composition of the copolymer was determined using elemental analysis. The obtained nitrogen content was 6.2% equivalent to 20.8 weight % or 26.7 mole % of vinylimidazole in the divinylbenzene-vinylimidazole copolymer. Yield was 22 g. The obtained particles were spherical and they had a particle size distribution from 50 to 150 μm (FIG. 1). The specific surface—determined by BET nitrogen adsorption method—was 509 m²/g. Total pore volume was 1.3 ml/g comprising 0.25 ml/g micropores, 0.75 ml/g mesopores, and 0.3 ml/g macropores in 1 g of the copolymer.

EXAMPLE 2

Determination of Bilirubin Adsorption

The suitability of the adsorbent material of this invention for extracorporeal blood purification was tested with a static and a dynamic bilirubin adsorption test and the results evaluated in comparison with conventionally used activated charcoal adsorbents. It is known that human albumin exceptionally strongly binds to bilirubin. Therefore, the adsorption behaviour of various adsorbents is observed with respect to bilirubin-human albumin complexes as a representation for numerous other albumin bound blood toxins and poisons.

Bilirubin is a degradation product of hemoglobin (red blood color) and is contained in bile colors. People with jaundice have an increased level of bilirubin which causes the characteristic yellow color of these patients. Normally, bilirubin is created in the spleen by oxidative cleavage of the porphyrine ring of heme followed by hydration of the green intermediate product biliverdin. As a decoupling agent of oxidative phosphorylization bilirubin is highly toxic for the organism and it is therefore bound to serum albumin in the blood circuit and transported to the liver. In patients with acute liver failure the liver cannot free the albumin from bilirubin. This function of the liver is to be replaced by selective adsorbents in perfusion techniques and a selective membrane in the MARS process.

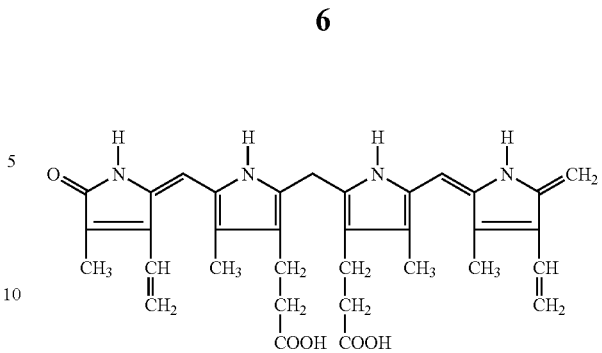

Structure of Bilirubin

Preparation of the Test Solution

Analogous to the environment in the human organism bilirubin was complexed with human serum albumin in a first step and this complex named B-HSA solution. To do so, 33 mg Bilirubin were weighed in a reaction vessel and dissolved within 5 min in 1.25 ml 0.1 m NaOH in an ultrasonic bath protected from light. After dissolution the content of the vessel were transferred quantitatively into a brown 100 ml flask which contained 28 ml of 20% HSA solution (Aventis GmbH, Germany) and 84 ml of 0.9% NaCl in water. The prepared bilirubin solution contains 5 weight % albumin and 504 μmol bilirubin per liter B-HSA solution.

Conditioning the Adsorbent Materials 500 mg of dry adsorbent material were weighed into a solid phase extraction (SPE) cartridge and placed on an SPE vacuum manifold. The adsorbent material is rinsed consecutively with two times 5 ml 70% ethanol, five times with 5 deionized water and eventually tree times with 0.9% NaCl solution and then dried for 2 minutes.

Static Bilirubin Adsorption Test (Batch Method)

500 mg of the conditioned adsorbent material were placed in a vessel and 5 ml B-HSA solution added. Then the vessel was shaken intensively on a laboratory shaker. In intervals of 15, 60, and 120 minutes the shaker was stopped to draw a 100 μl sample of the overlaying solution for UV spectroscopic bilirubin determination. The sample was diluted with 0.9 ml of 0.9% NaCl solution and analyzed in an 0.2 cm cuvette.

Determination of the remaining bilirubin concentration is performed at the long wavelength absorption maximum at 453 nm. Changes of the extinction of this band correspond to changes of bilirubin concentration in the B-HSA solution. The extinction of the B-HSA solution before contact with the adsorbent material was used as a reference value. This way, relative concentration changes can be easily determined. The remaining bilirubin concentration was usually given as three percent values corresponding to the concentration after 15, 60, and 120 minutes. The reference B-HSA solution contains 5% human serum albumin and 505 μmol/l bilirubin. Results are shown in FIG. 2a.

Dynamic Bilirubin Adsorption Test (Circuit Method)

A dynamic bilirubin adsorption test was developed in order to compare the adsorbent material of this invention with activated charcoal which is currently typically used in medicine. This test tries to simulate the conditions present in a conventional perfusion method or in a MARS device. To do so, the adsorbent material is placed in solid phase extraction cartridges ("mini cartridges") and placed on a vacuum manifold. The adsorbent is conditioned as described above and then loaded with B-HSA solution. When applying soft vacuum the solution flows through the adsorbent material and bilirubin concentration was determined in the filtrate by UV spectroscopy. The filtrate was then returned to the top of the cartridge and the procedure repeated 7 times. Results are shown in FIG. 2b.

COMPARATIVE EXAMPLE

Figure 2:
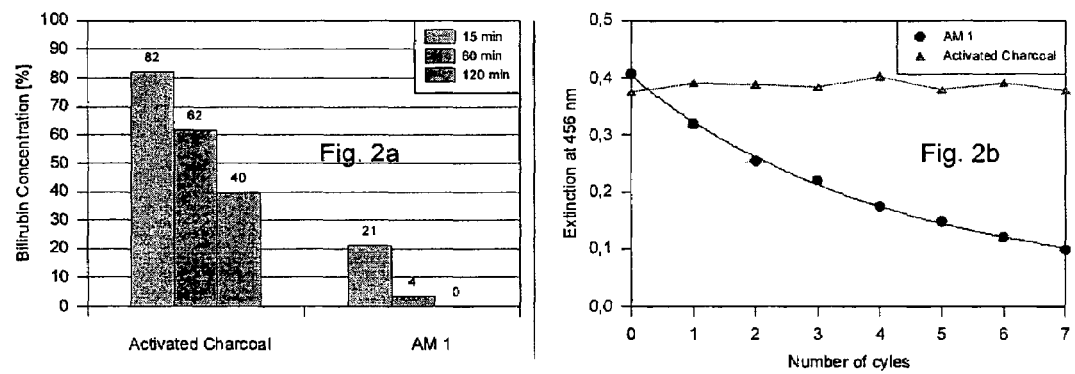
FIGS. 2a and 2b are graphs showing the results of static and dynamic bilirubin absorption tests, respectively, using activated charcoal and the inventive absorbent particles.

In order to compare the adsorption properties of the adsorbent material of this invention the currently used medical activated charcoal was conditioned in and tested in both the static and dynamic bilirubin adsorption test. FIG. 2 shows the behaviour of the activated charcoal and the adsorbent material of this invention in the static and dynamic tests side by side.

The adsorption speed of the adsorbent material of this invention is much higher than of the currently used activated charcoal (static test, FIG. 2a). Within 1 hour Activated charcoal adsorbs ca. 60% of the bilirubin from the B-HSA solution. In contrast to this, the adsorbent material adsorbs almost all (98-100%) of the bilirubin under the same conditions.

The advantage of the adsorbent material is even clearer in the dynamic test (FIG. 2b). While activated charcoal can hardly adsorb any bilirubin under dynamic conditions the adsorbent material of this invention shows an exponential decrease of bilirubin concentration. After 7 cycles through the adsorbent bed the relative bilirubin concentration in the filtrate is 25%. This result gives hope to a significant reduction of treatment times, an increase of effectivity, and an increase of the survival rate of patients with acute liver failure.

EXAMPLE 3

200 mg of adsorbent material AM1 were weighed into a 6 ml SPE cartridge and conditioned with 5 ml of 70 weight % ethanol, 5 ml distilled water and 5 ml 0.9% NaCl solution. The conditioned adsorbent material was then loaded with 2 ml of a bile acids solution (c=1 mg/ml) in 0.9% NaCl solution. 20 µl of the eluate were then injected on a GPC column (HEMA 2000, PSS Standards Service GmbH, Mainz, Germany), eluted with 0.9% NaCl solution and detected with an RI detector. Loading with bile acids solution was repeated until the chromatogram showed a signal for bile acids. From the number of load steps until this event the capacity of adsorbent material could be determined to be 210 mg bile acids per gram adsorbent material AM1.

What is claimed is:

1. An adsorbent material, based on crosslinked, porous imidazole-divinylbenzene copolymers, for application in blood-, blood plasma-, and albumin purification processes, said adsorbent material being formed by radical suspension polymerization of a monomer mixture of divinylbenzene crosslinker and an imidazole derivative, wherein
   the polymerization is conducted in the presence of air and/or oxygen, a salt, a stabilizer, and an inert substance;
   the adsorbent material contains 5 weight % to 30 weight % of the imidazole derivative;
   the adsorbent material has a specific surface from 200 m$^2$/g to 900 m$^2$/g and a total pore volume from 1.0 cm$^3$/g to 2.0 cm$^3$/g where 1 g of the material contains up to 0.3 cm$^3$ micropores, up to 1.2 cm$^3$ mesopores, and up to 0.5 cm$^3$ macropores; and
   the adsorbent material is essentially of spherical shape having a particle size range from 1 µm to 300 µm and an average pore diameter in the range of 100 Å to 500 Å.

2. The adsorbent material of claim 1 where the divinylbenzene copolymer comprises 50 weight % to 85 weight % of isomeric divinylbenzene and 5 weight % to 40 weight % of isomeric ethylvinylbenzene.

3. The adsorbent of claim 1 comprising predominantly spherical particles having a particle size from 50 µm to 200 µm.

4. The adsorbent material of claim 1 where the radically polymerizable imidazole derivative are 1-vinylimidazole, 4-vinylimidazole, 1-vinyl-2-methylimidazole, 1-vinyl-2-ethylimidazole, 1-propenyl-2-imidazole, 1-allyl-2-methylimidazole, exclusively or mixtures thereof, or an unsubstituted imidazole monomer.

5. The adsorbent of claim 1 comprising predominantly spherical particles having a particle size from 1 µm to 50 µm.

6. A method of suspension polymerization to produce the adsorbent material of claim 1 where the aqueous phase comprises 5 weight % to 25 weight % of a salt and 0.5 weight % to 5 weight % of a suspension stabilizer, the organic phase comprises 25 weight % to 50 weight % of an inert substance, and the polymerization is conducted in the presence of air and/or oxygen.

7. The method of claim 6 where the inert substance comprises toluene, ethyl acetate, butyl acetate, dichlorethane, or carbon tetrachloride, exclusively.

8. The method of claim 6 where the suspension stabilizer comprises poly(vinyl alcohol) or methyl cellulose or hydroxyethyl cellulose or calcium phosphate or aluminium hydroxide or magnesium hydroxide.

9. The method of claim 6 where the inert substance comprises a mixture of at least two inert substances selected from the group consisting of toluene, ethyl acetate, butyl acetate, dichlorethane, and carbon tetrachloride.

10. A method of blood purification in plasma- or blood purification processes comprising:
   (a) providing an adsorbent material based on crosslinked, porous imidazole-divinylbenzene copolymers, said adsorbent material being formed by specific radical suspension polymerization of a monomer mixture in the presence of air and/or oxygen, a salt, and an inert substance, said adsorbent material comprising at least 50 weight percent divinylbenzene crosslinker and 4 to 30 weight percent of an imidazole derivative, said adsorbent material being highly crosslinked and highly porous, said adsorbent material having a spherical shape and specific characteristics of surface, pore size distribution, pore diameter, and particle size range, for application in blood-, blood plasma-, and albumin purification processes, where said adsorbent material has an average pore diameter in the range of 100 Å to 500 Å and 1 g of the material contains up to 0.3 cm$^3$ micropores, up to 1.2 cm$^3$ mesopores, and up to 0.5 cm$^3$ macropores; and
   (b) applying the adsorbent material to blood or blood plasma.

11. A method of blood purification comprising:
   (a) providing an adsorbent material based on crosslinked, porous imidazole-divinylbenzene copolymers, said adsorbent material being formed by specific radical suspension polymerization of a monomer mixture in the presence of air and/or oxygen, a salt, and an inert substance, said adsorbent material comprising at least 50 weight percent divinylbenzene crosslinker and 4 to 30 weight percent of an imidazole derivative, said adsorbent material being highly crosslinked and highly porous, said adsorbent material having a spherical shape and specific characteristics of surface, pore size distribution, pore diameter, and particle size range, for application in blood-, blood plasma-, and albumin purification processes, where said adsorbent material has an average pore diameter in the range of 100 Å to 500 Å and 1 g of the material contains up to 0.3 cm$^3$ micropores, up to 1.2 cm$^3$ mesopores, and up to 0.5 cm$^3$ macropores; and (b) applying the adsorbent material to blood in a Molecular Adsorbent Recirculating System (MARS).

12. A method of blood purification comprising:

(a) providing an adsorbent material based on crosslinked, porous imidazole-divinylbenzene copolymers, said adsorbent material being formed by specific radical suspension polymerization of a monomer mixture in the presence of air and/or oxygen, a salt, and an inert substance, said adsorbent material comprising at least 50 weight percent divinylbenzene crosslinker and 4 to 30 weight percent of an imidazole derivative, said adsorbent material being highly crosslinked and highly porous, said adsorbent material having a spherical shape and specific characteristics of surface, pore size distribution, pore diameter, and particle size range, for application in blood-, blood plasma-, and albumin purification processes, where said adsorbent material has an average pore diameter in the range of 100 Å to 500 Å and 1 g of the material contains up to 0.3 cm$^3$ micropores, up to 1.2 cm$^3$ mesopores, and up to 0.5 cm$^3$ macropores; and (b) applying the adsorbent material to blood as a sorbent for bilirubin and bile acids.

* * * * *